US011766186B2

(12) United States Patent
Mantrawadi et al.

(10) Patent No.: US 11,766,186 B2
(45) Date of Patent: Sep. 26, 2023

(54) WEARABLE DEVICE WITH FIELD REPLACEABLE BAND

(71) Applicant: AMAZON TECHNOLOGIES, INC., Seattle, WA (US)

(72) Inventors: Manish Avinash Mantrawadi, Redmond, WA (US); Benjamin Douglas Garcia, Seattle, WA (US); Maya Shirish Sathaye, Seattle, WA (US); Kelly Erin Johnson, Oakland, CA (US); Simon Quay, Portland, OR (US)

(73) Assignee: AMAZON TECHNOLOGIES, INC., Seattle, WA (US)

( * ) Notice: Subject to any disclaimer, the term of this patent is extended or adjusted under 35 U.S.C. 154(b) by 1065 days.

(21) Appl. No.: 16/352,195

(22) Filed: Mar. 13, 2019

(65) Prior Publication Data

US 2020/0289001 A1 Sep. 17, 2020

(51) Int. Cl.
*A61B 5/024* (2006.01)
*A61B 5/00* (2006.01)

(52) U.S. Cl.
CPC ...... *A61B 5/02438* (2013.01); *A61B 5/02427* (2013.01); *A61B 5/681* (2013.01);
(Continued)

(58) Field of Classification Search
CPC ............... A61B 5/02427; A61B 5/681; A61B 2560/0443; A61B 2562/0219;
(Continued)

(56) References Cited

U.S. PATENT DOCUMENTS 2,937,744 A    5/1960   Olson
4,813,459 A *   3/1989   Breidegam .............. A61N 1/14
139/420 C (Continued)

OTHER PUBLICATIONS

Tang, Xiaofan "Patent Cooperation Treaty International Preliminary Report on Patentability and Written Opinion dated Aug. 25, 2021", Patent Cooperation Treaty Application No. PCT/US2020/021905, Patent Cooperation Treaty, Aug. 25, 2021.

(Continued)

*Primary Examiner* — Oommen Jacob
(74) *Attorney, Agent, or Firm* — Lindauer Law, PLLC

(57) ABSTRACT

A wearable device has a housing containing electronics and a band that retains the wearable device on a user's arm. Each end of the housing has a receptacle with a ridge around the opening of the receptacle. A band comprises a strip of flexible material. A pair of protrusions with enlarged ends made from an elastomeric material extend from an inner surface of the band. A portion of the inner surface of the band between the protrusions is in contact with at least a portion of an upper surface of the housing. The band is joined to the housing by aligning each protrusion with a corresponding receptacle and applying pressure. As a result of the applied pressure part of the protrusion temporarily deforms, enters the receptacle, and resumes substantially the previous shape thus holding the protrusion within the receptacle and the band to the housing.

20 Claims, 10 Drawing Sheets

(52) U.S. Cl.
CPC ............... *A61B 2560/0443* (2013.01); *A61B 2562/0219* (2013.01); *A61B 2562/164* (2013.01)

(58) Field of Classification Search
CPC ............ A61B 2562/164; A61B 5/021; A61B 5/14551; A61B 5/02438; A45F 5/00; A45F 2005/008
See application file for complete search history.

(56) References Cited

U.S. PATENT DOCUMENTS

| | | | | |
|---|---|---|---|---|
| 4,825,879 | A * | 5/1989 | Tan | A61B 5/02427 600/490 |
| 5,623,933 | A * | 4/1997 | Amano | A61B 5/0053 600/500 |
| 5,638,818 | A * | 6/1997 | Diab | A61B 5/02427 600/479 |
| 6,012,203 | A * | 1/2000 | Baron Pearson | A43B 23/24 24/114.9 |
| 6,792,300 | B1 * | 9/2004 | Diab | A61B 5/6838 600/344 |
| 8,328,055 | B1 | 12/2012 | Snyder | |
| 9,311,686 | B2 | 4/2016 | Roush et al. | |
| 9,575,466 | B1 * | 2/2017 | Thompson | G04B 47/06 |
| 10,542,794 | B2 * | 1/2020 | McCray | A44C 5/0007 |
| 10,575,602 | B2 * | 3/2020 | Perkins | A44B 11/263 |
| 10,606,313 | B2 * | 3/2020 | VanDuyn | G06F 1/1635 |
| 10,691,072 | B1 * | 6/2020 | Johnson | G04B 37/1486 |
| 11,226,652 | B2 * | 1/2022 | Liu | H01R 13/2471 |
| 2005/0168340 | A1 * | 8/2005 | Mosher, Jr. | G06K 19/07749 340/572.7 |
| 2005/0253047 | A1 | 11/2005 | Maegawa et al. | |
| 2011/0094876 | A1 | 4/2011 | Liang | |
| 2014/0107493 | A1 * | 4/2014 | Yuen | A61B 5/0022 600/479 |
| 2015/0265034 | A1 | 9/2015 | Lee et al. | |
| 2015/0296963 | A1 | 10/2015 | Byun et al. | |
| 2015/0346877 | A1 | 12/2015 | Justice et al. | |
| 2016/0058375 | A1 | 3/2016 | Rothkopf | |
| 2016/0235132 | A1 | 8/2016 | Sugano et al. | |
| 2018/0013947 | A1 * | 1/2018 | Kim | G06F 1/163 |
| 2018/0059714 | A1 * | 3/2018 | Martin | G06F 1/1635 |
| 2018/0103733 | A1 * | 4/2018 | Trahern | A44C 9/02 |
| 2020/0289001 | A1 * | 9/2020 | Mantrawadi | A45F 5/00 |

OTHER PUBLICATIONS

Perrin, Maggie, "Invitation to Pay Additional Fees dated May 7, 2020", Patent Cooperation Treaty Application No. PCT/US20/21905, Patent Cooperation Treaty, May 7, 2020.

* cited by examiner

WEARABLE DEVICE WITH FIELD REPLACEABLE BAND

BACKGROUND

Wearable devices may be affixed to a user with a band. For example, a watch may be held on a user's wrist with a watchband.

BRIEF DESCRIPTION OF FIGURES

The detailed description is set forth with reference to the accompanying figures. In the figures, the left-most digit(s) of a reference number identifies the figure in which the reference number first appears. The use of the same reference numbers in different figures indicates similar or identical items or features.

Figure 1:
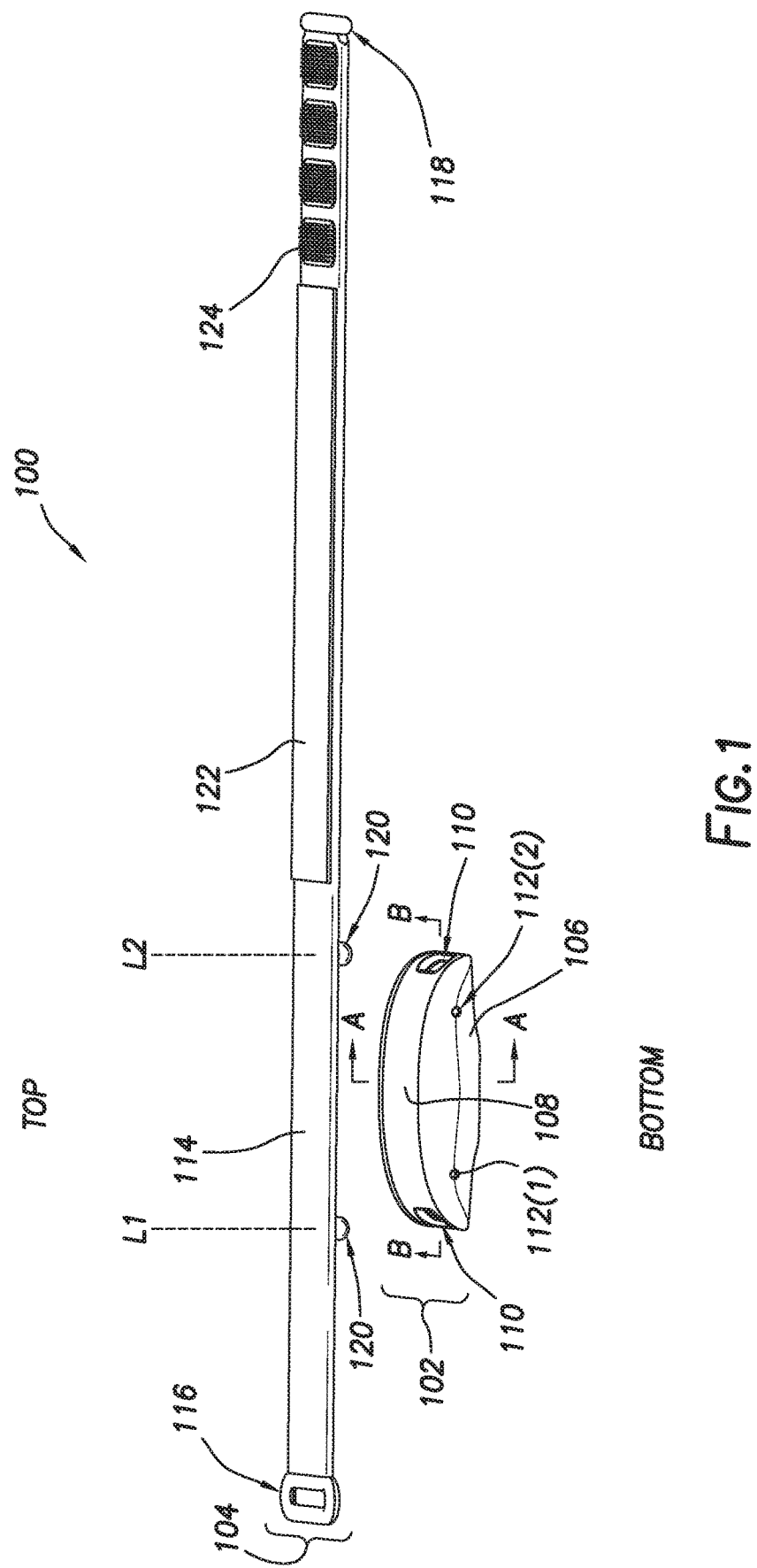
FIG. 1 is an illustrative wearable device comprising a housing and a field replaceable band, according to one implementation.

While implementations are described herein by way of example, those skilled in the art will recognize that the implementations are not limited to the examples or figures described. It should be understood that the figures and detailed description thereto are not intended to limit implementations to the particular form disclosed but, on the contrary, the intention is to cover all modifications, equivalents, and alternatives falling within the spirit and scope as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean "including, but not limited to".

The structures depicted in the following figures are not necessarily according to scale. Furthermore, the proportionality of one component to another may change with different implementations. In some illustrations the scale or a proportionate size of one structure may be exaggerated with respect to another to facilitate illustration, and not necessarily as a limitation.

DETAILED DESCRIPTION

A wearable device may be used to provide a variety of functions to a user. These functions may include providing information, acquiring data using sensors, and so forth. The wearable device may operate alone or may utilize a communication link to operate in conjunction with another device such as a smartphone.

The wearable device may include output devices such as a haptic buzzer that provides haptic feedback to the user, a speaker to provide audio output, a light emitting diode (LED) to provide a visual indicator, and so forth.

The sensors on the wearable device may acquire data that helps the user perform various functions. For example, the wearable device may include a microphone, allowing the user to provide speech input to an application running on the smartphone. Other sensors such as accelerometers, heart rate monitors, and so forth may be used to acquire data about the user's activity level, physical condition, and so forth. This data may then help the user. For example, information about how much the user is moving may be compared to a goal and used to provide an output that informs the user and helps them increase their activity level.

The wearable device may include two parts: a housing and a band. The housing contains at least some of the electronics of the wearable device, such as the output devices and the sensors. The housing may be sealed to prevent water, dirt, or other foreign materials from entering the housing.

The band retains the housing proximate to the user. In some implementations a bottom surface of the housing may be in contact with the user's skin. Various sizes and types of band may be used, allowing for the housing to be worn on an arm, leg, abdomen, neck, and so forth. For example, the wearable device may be worn as a wristband, with the band holding the housing near the user's wrist. In another example, the wearable device may be worn as an anklet, with the band holding the housing near the user's ankle.

It is advantageous to be able to affix different bands to a given housing. Different bands may be chosen for one or more of aesthetic or functional reasons depending on the situation. For example, a band what is waterproof may be selected when the user expects to be in a wet environment. In another example, a band that is decorative may be selected when the user is going to be socializing. In another example, a band made from a specific material may be selected by a user to avoid contact dermatitis. In still another example, a band may become worn and require replacement.

The combination of the band and the housing should also be comfortable for extended wear. For example, the user should be able to wear the wearable device without experiencing pinching, gouging, undue pressure, and so forth.

Traditional mechanisms for affixing a band to a device may utilize various arrangements, such as spring-loaded pins or a "NATO" style watch strap in which the band passes through loops. Spring-loaded pins and other arrangements require the use of tools and significant dexterity to join or separate the band from the device. As a result, a user may be unable to easily change the band, limiting the frequency and utility of the wearable device. The NATO style watch strap and other arrangements require that the strap be relatively thin to pass through the loops, constraining the types of bands that may be used. The NATO style watch strap also places the band between the device and the user's skin. This placement precludes the use of sensors in the device that require contact with or a view of the user's skin to operate. For example, an optical heart rate monitor that uses reflected light to measure the user's pulse cannot operate through a nylon NATO style watch strap.

Described in this disclosure is a wearable device that allows for easy and tool-free removal and installation of a band, with respect to a housing. Removal and installation may be performed by a user with limited physical dexterity. As described in this disclosure, a housing may comprise one or more receptacles. For example, the housing may include a pair of receptacles with one on each end of the housing. The opening for each receptacle is in an upper surface of the housing. During wear, a bottom surface of the housing is in contact with at least a part of the user. A retention ridge extends around a perimeter of the opening for each receptacle. As a result, the entrance to the receptacle is smaller along at least one dimension than the interior volume of the receptacle.

One or more pairs of protrusions extend from an inner surface of the band. For example, when the housing includes a pair of receptacles a pair of protrusions extend from the band. The protrusions may comprise an elastomeric material, such as silicone rubber. Each of these protrusions have an enlarged tip, presenting a bulbous profile. The enlarged portion of the tip is slightly larger than the entrance to the receptacle. The band is affixed to the housing by placing the inner surface of the band in contact with the upper surface of the housing. A protrusion is aligned to a receptacle, and the user applies a force to the band on the outer surface opposite the protrusion. The applied force causes the enlarged tip of the protrusion to deform, allowing it to pass into the receptacle. Once within the receptacle, the elastomeric material expands, securing part of the protrusion within the receptacle and thus the band to the housing. In some implementations an audible "pop" or other sound is produced, providing audible feedback to the user that the band and the housing have been adequately engaged.

The band may then be wrapped around an arm and secured using a hook and loop fastener. Once the band has been secured, the wearable device is securely retained on the arm of the user.

To separate the band from the housing, the process is reversed. The user unwraps the band from their arm and pulls the band to withdraw the protrusions from their respective receptacles. In some implementations an audible "pop" or other sound is produced, providing audible feedback to the user that the band and the housing have been separated.

Also described are the structures and techniques for joining the housing to an upper cover that seals an opening in the housing. A groove extends around an opening in the housing. Adhesive is placed within the groove. A first ridge extends from an inner surface of the upper cover. Upon installation, at least a portion of the first ridge is placed into the groove. A second ridge may also extend from the inner surface of the upper cover proximate to the perimeter of the opening. A gasket may also be employed between the second ridge and the housing. The upper cover may also include a lip on each end. When installed, each lip engages a corresponding recess on the end of the housing.

Illustrative System

FIG. 1 is an illustrative view of a wearable device 100, according to one implementation. The wearable device 100 comprises a housing 102 and a band 104. The housing 102 may comprise a body 106 and an upper cover 108. The body 106, upper cover 108, and other components may comprise one or more of a metal, plastic, composite, ceramic, and so forth.

The body 106 may include one or more openings. For example, during assembly components may be placed within the body 106 through an opening that is then closed by the upper cover 108. The body 106 and the upper cover 108 may be joined such that the resulting housing 102 is sealed. In the implementation shown here, an upper surface of the housing 102 is curved. During wear, the upper surface of the housing 102 faces away from the portion of the user to which the wearable device 100 is retained. A lower surface of the housing 102 is proximate to the portion of the user. For example, at least a portion of the lower surface may be in contact with the user while the wearable device 100 is being worn.

The body 106 includes one or more receptacles 110. As illustrated here, the body 106 is generally rectangular when viewed from above, with two ends. In the implementation depicted here a first receptacle 110 is proximate to a first end of the body 106 while a second receptacle 110 is proximate to a second end of the body 106. Each receptacle 110 has an opening on the upper surface of the housing 102. For example, the receptacle 110 may be within the body 106 while the upper cover 108 includes apertures for each of the openings of the receptacles 110.

Each receptacle 110 is configured such that the opening or entry to the receptacle 110 is smaller along at least one dimension than an interior volume of the receptacle 110. For example, each receptacle 110 may include a retention ridge that is proximate to the opening in the receptacle 110. The retention ridge introduces a constriction or narrowing. For example, in cross-section the receptacle 110 may appear to resemble a mushroom shape with a root or stalk that is narrower than a larger, bulbous tip. In some implementations the retention ridge may extend along the entire perimeter of the opening.

The housing 102 may include one or more apertures 112. The body 106 may include several apertures 112 for microphone ports, light emitting diodes, air pressure sensors, and so forth. In this view, apertures 112(1) and 112(2) are shown on a first side of the housing 102. For example, the aperture 112(1) may comprise a pressure equalization port and the aperture 112(2) may provide a port for a first microphone to receive sound from outside the housing 102.

The band 104 may comprise a flexible member 114 having a first end and a second end. The flexible member 114 includes an inner surface and an outer surface. When the band 104 is affixed to the housing 102, at least a part of the inner surface of the flexible member 114 is proximate to the upper surface of the housing 102.

The flexible member 114 may comprise one or more of fabric, an elastomeric material, a plurality of links, and so forth. For example, the flexible member 114 may comprise an elastic fabric. A loop 116 may be arranged at the first end of the flexible member 114 while an endcap 118 is arranged at the second end. The loop 116 may be a rigid loop. For example, the loop 116 may comprise metal that is encased in plastic. In other implementations, the loop 116 may comprise a flexible material.

One or more protrusions 120 extend away from the inner surface of the flexible member 114. In the implementation shown here, a first protrusion 120 extends from the inner surface of the flexible member 114 at a first location L1 and a second protrusion 120 extends from the inner surface at a second location L2.

Each protrusion 120 is configured to maintain mechanical engagement after insertion into the receptacle 110. The protrusions 120 may comprise an elastomeric material. In one implementation, the protrusions 120 may comprise silicone rubber having a hardness as measured using a durometer with a Shore A reading of between 70 and 90.

In one implementation, the protrusions 120 may comprise components that have been joined to the flexible member 114. For example, the protrusions 120 may be formed and then joined to the flexible member 114 using one or more of an adhesive, mechanical fasteners, thread, and so forth.

In another implementation the protrusions 120 may be integral with at least a portion of the flexible member 114. For example, the flexible member 114 and the protrusions 120 may comprise a unitary piece of elastomeric material.

A portion of each protrusion 120 is larger than the narrowest part of the opening into the receptacle 110. For example, a first distance D1 indicates the maximum width of the opening in the receptacle 110. A second distance D2 indicates the maximum interior width of interior space of the receptacle 110 at the widest point. Due to the constriction in the receptacle 110, the first distance D1 is less than the second distance D2.

A third distance indicates the maximum width of the protrusion 120 at its widest point. The third distance is greater than the first distance D1. For example, at the widest point the bulbous tip of the protrusion 120 is larger than the opening of the receptacle 110. In one implementation, the third distance of the maximum width of the protrusion 120 may be at least 15% greater than the first distance D1.

In one implementation the third distance may be less than the second distance D2. For example, the widest point of the protrusion 120 may be smaller than the largest width of the receptacle 110. In another implementation the uncompressed protrusion 120 may have a third distance that is greater than the second distance D2. For example, after insertion into the receptacle 110 the protrusion 120 may expand and exert some pressure on the interior surface of the receptacle 110 as the elastomeric material attempts to resume a prior shape. In this implementation the portion of the protrusion 120 that is within the receptacle 110 remains at least slightly compressed.

In the implementation depicted here, the each of the two protrusions 120 extending from the inner surface of the flexible member 114 has a corresponding receptacle 110. The band 104 is affixed to the housing 102 by placing the inner surface of the flexible member 114 in contact with the outer surface of the upper cover 108, placing the band 104 atop the housing 102. For example, the inner surface of the flexible member 114 between L1 and L2 may be in contact with the upper cover 108.

Each protrusion 120 is aligned to a respective receptacle 110 and a force is applied to the flexible member 114 on the outer surface opposite the protrusion 120. The applied force causes the enlarged portion of the protrusion 110 to temporarily deform, allowing it to pass into the cavity of the receptacle 110. In some implementations an audible "pop" or other sound is produced, providing audible feedback to the user that the band 104 and the housing 102 have been adequately engaged. Once within the receptacle 110, the elastomeric material expands, securing part of the protrusion 120 within the receptacle 110. The band 104 is now affixed to the housing 102.

To separate the band 104 from the housing 102, the process is reversed. A pull may be applied to the flexible member 114. Under the influence of the pull, the protrusion 120 temporarily deforms and is able to be withdrawn from the receptacle 110. In some implementations an audible "pop" or other sound is produced, providing audible feedback to the user that the band 104 and the housing 102 have been separated.

In one implementation, the one or more receptacles 110 in the housing 102 may be configured with the same dimensions. Likewise, the one or more protrusions 120 on the band 104 may be configured with the same dimensions. In this implementation, the relative orientation of the housing 102 with respect to the band 104 may be easily changed. For example, a left-handed user may wish to reverse the orientation of the housing 102 with respect to the band 104 to allow improved access to one or more controls on the housing 102. In other implementations the dimensions of one or more of the receptacles 110 or the protrusions 120 may differ, enforcing a particular orientation of the band 104 with respect to the housing 102.

Instead of an elastomeric material, the protrusions 120 may comprise a one or more spring elements. For example, the protrusions 120 may comprise a metal or plastic element that forms a living hinge. In another example, the protrusions 120 may comprise one or more features that are biased using one or more compression springs.

With the housing 102 and the band 104 attached, the wearable device 100 may be worn by a user. The flexible member 114 may include on the outer surface a loop portion 122 comprising a plurality of loops and a hook portion 124 comprising a plurality of hooks. To affix the wearable device 100 to the user, the second end of the flexible member 114 having the endcap 118 is passed through the loop 116. The user may place their forearm into the loop formed by the flexible member 114. The second end of the flexible member 114 may then be pulled such that the inner surface is in comfortable contact with the user's forearm, and the hook portion 124 is then pressed against the loop portion 122, securing the flexible member 114.

In other implementations, other mechanisms may be used to secure the wearable device 100 to the user. For example, the flexible member 114 may utilize a buckle, a folding clasp, butterfly closure, and so forth. In another example, the flexible member 114 may comprise a contiguous loop of elastomeric material, allowing the user to pass their hand through the loop and which then contracts to hold the wearable device 100 in place.

At least a portion of the flexible member 114 between the first location L1 and the second location L2 may comprise an elastomeric material. A distance between the receptacles 110 may be slightly greater than the distance between L1 and L2. In this implementation, during and after installation the portion of the band 104 between L1 and L2 is under tension from the elastomeric material of the flexible member 114 attempting to resume a prior shape. This tension provides a biasing force that assists in keeping the inner surface of the flexible member 114 in contact with the upper surface of the housing 102. By maintaining contact, the flexible member 114 is not wrinkled or otherwise protruding, thus preventing snags, preventing contaminants from accumulating in between the two, and improving the aesthetics of the wearable device 100.

In some implementations the housing 102 may include one or more output devices on the upper surface. For example, a display device may be arranged on the upper surface between the receptacles 110 to provide visual output to the user. At least a portion of the flexible member 114 that is between the first location L1 and the second location L2 may be transparent, contain one or more holes, or another opening to allow at least a portion of the display device to be visible. For example, the flexible member 114 may comprise a transparent material such as silicone rubber. In another example, the flexible member 114 may comprise an opening or aperture that is coincident with the display device. In another example, the flexible member 114 may comprise a plurality of holes, perforations, or spaces between threads that allow at least a portion of light from the display device to pass through.

Figure 2:
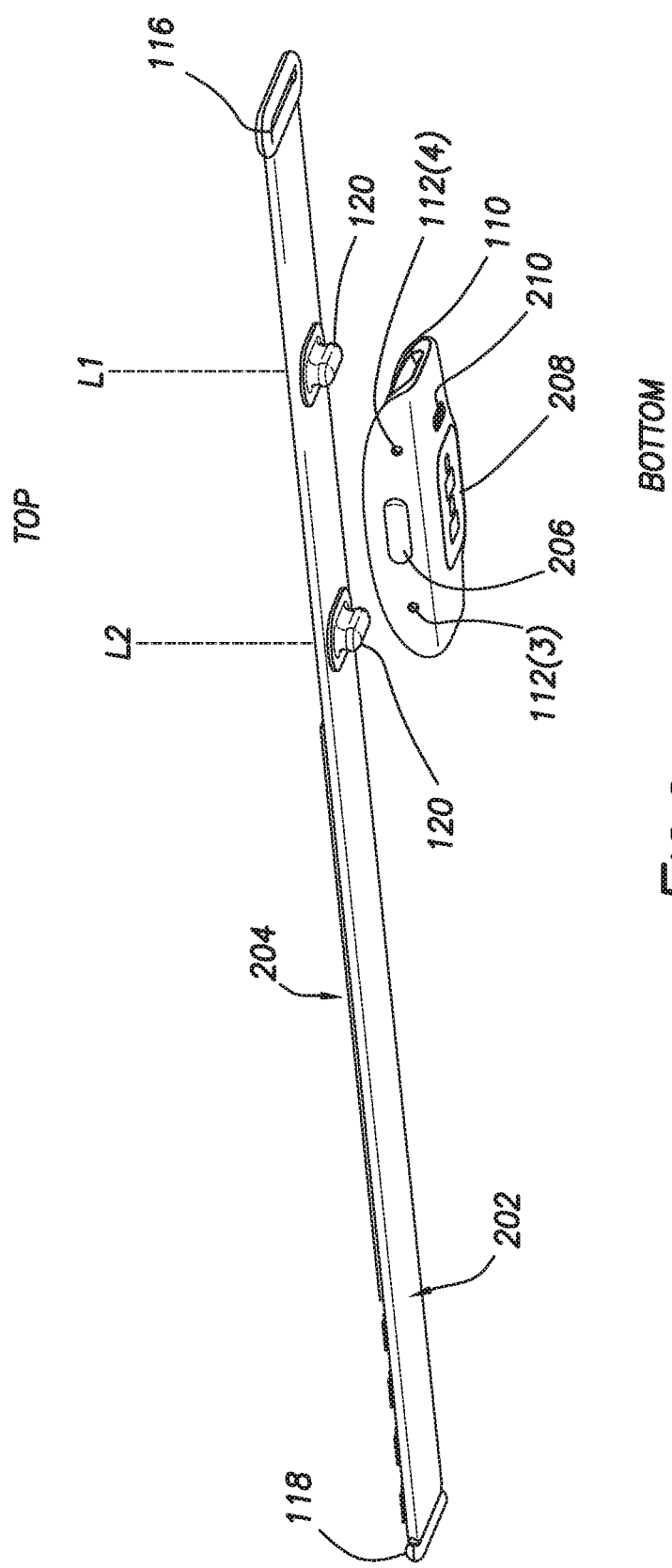
FIG. 2 is another view of the wearable device of FIG. 1 showing the protrusions on the band and corresponding receptacles in the housing, according to one implementation.

FIG. 2 is another view of the wearable device 100 of FIG. 1 with the band 104 not yet affixed to the housing 102, according to one implementation. In this view, the inner surface 202 and the outer surface 204 of the flexible member 114 are shown. In this view additional apertures 112(3) and 112(4) are shown. For example, the aperture 112(3) may provide a path for light from an LED to exit the housing 102 while the aperture 112(4) may provide a port for a second microphone to receive sound from outside the housing 102.

A button 206 is also present on this side of the housing 102 between the apertures 112(3) and 112(4). The button 206 may be used to activate a switch to allow for user input.

A sensor window 208 is arranged on a bottom surface of the housing 102. The sensor window 208 may be transparent to one or more wavelengths of light. For example, the sensor window 208 may be transparent to visible and infrared light. The sensor window 208 may be used by one or more sensors to obtain information about the user. A field of view of one or more sensors may pass through the sensor window 208. For example, an optical heart rate monitor may comprise an LED that emits light which passes through the sensor window 208 and to the arm of the user. Reflected or scattered light returns through the sensor window 208 where it is measured by a photodetector. In another example a camera may have a field of view that passes through the sensor window 208 to obtain images of a portion of the user's arm.

In some implementations, the portion of the bottom surface of the housing 102 that includes the sensor window 208 may protrude away from the remainder of the bottom surface.

One or more electrical contacts 210 may also be present on the bottom surface of the housing 102. The electrical contacts 210 may be used to transfer data, provide electrical power, and so forth. In some implementations the electrical contacts 210 may be recessed with respect to the bottom surface.

Figure 3:
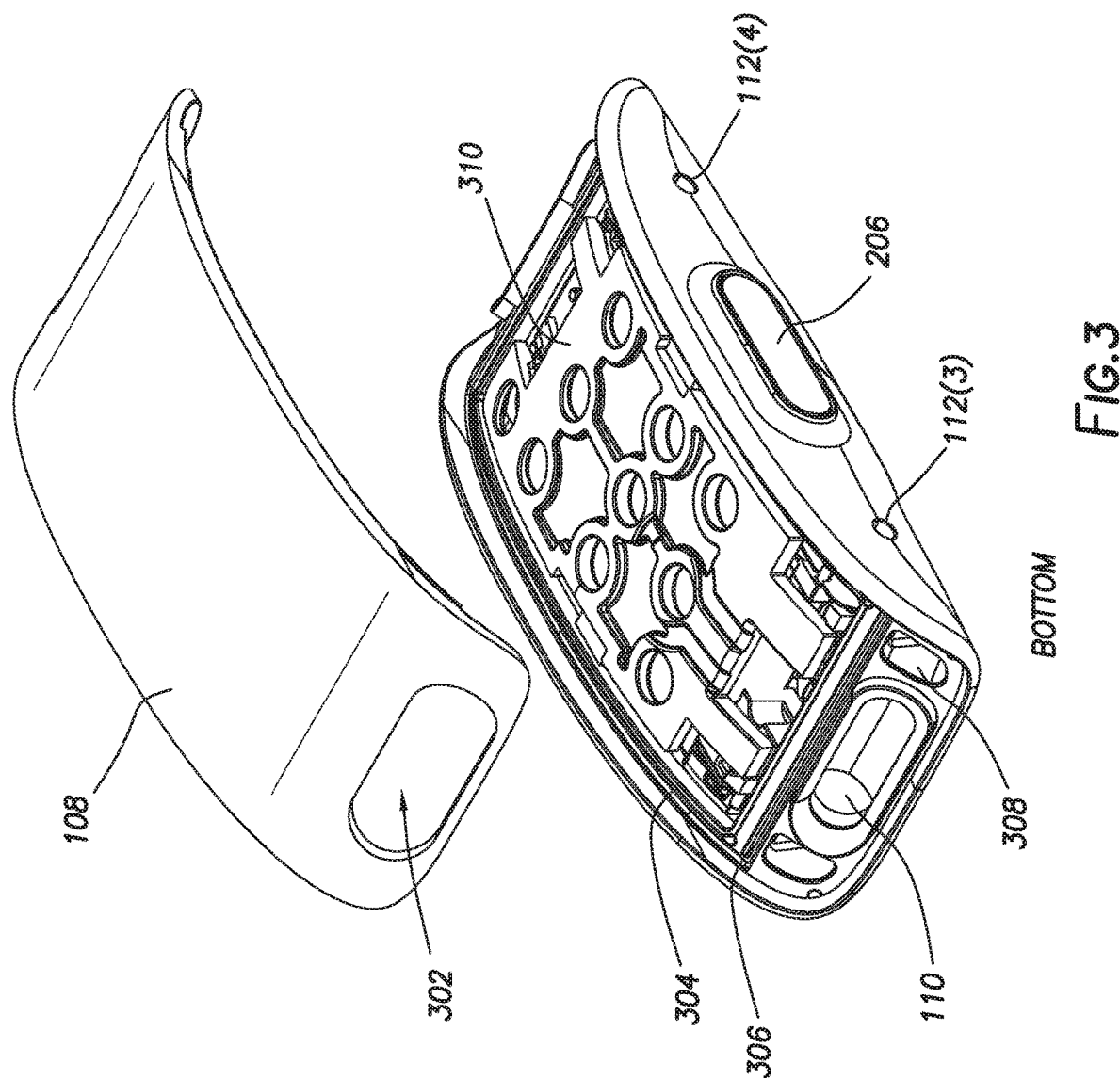
FIG. 3 is a perspective view of the housing of the wearable device prior to installation of an upper cover, according to one implementation.

FIG. 3 is a perspective view of the housing 102 of the wearable device 100 prior to installation of the upper cover 108, according to one implementation. The upper cover 108 may have one or more receptacle holes 302. The receptacle holes 302 provide clearance for the receptacle 110 when the upper cover 108 is joined to the housing 102.

A groove 304 extends around a perimeter of an upper portion of the housing 102. For example, the groove 304 is arranged around the opening into the interior of the housing 102. The upper cover 108 includes a ridge along an underside. To join the upper cover 108 and the housing 102, adhesive 306 may be placed into the groove 304. For example, a liquid dispense adhesive (LDA) may be dispensed into the groove 304. The upper cover 108 is placed onto the housing 102 and at least a portion of this ridge fits within the groove 304 and comes into contact with the adhesive 306. This interface is described in more detail with regard to FIGS. 6A and 6B.

The housing 102 may include one or more recesses 308 that retain excess adhesive 306 that may be displaced during assembly. For example, as the upper cover 108 is pressed down onto the housing 102, excess adhesive 306 may be displaced into the recesses 308.

Within the housing 102 an internal stiffener 310 is visible. The internal stiffener 310 provides mechanical support to the upper cover 108. The internal stiffener 310 may be fabricated as a separate piece and then joined to the upper cover 108. In other implementations the internal stiffener 310 and the upper cover 108 may comprise a single structure.

Figure 4:
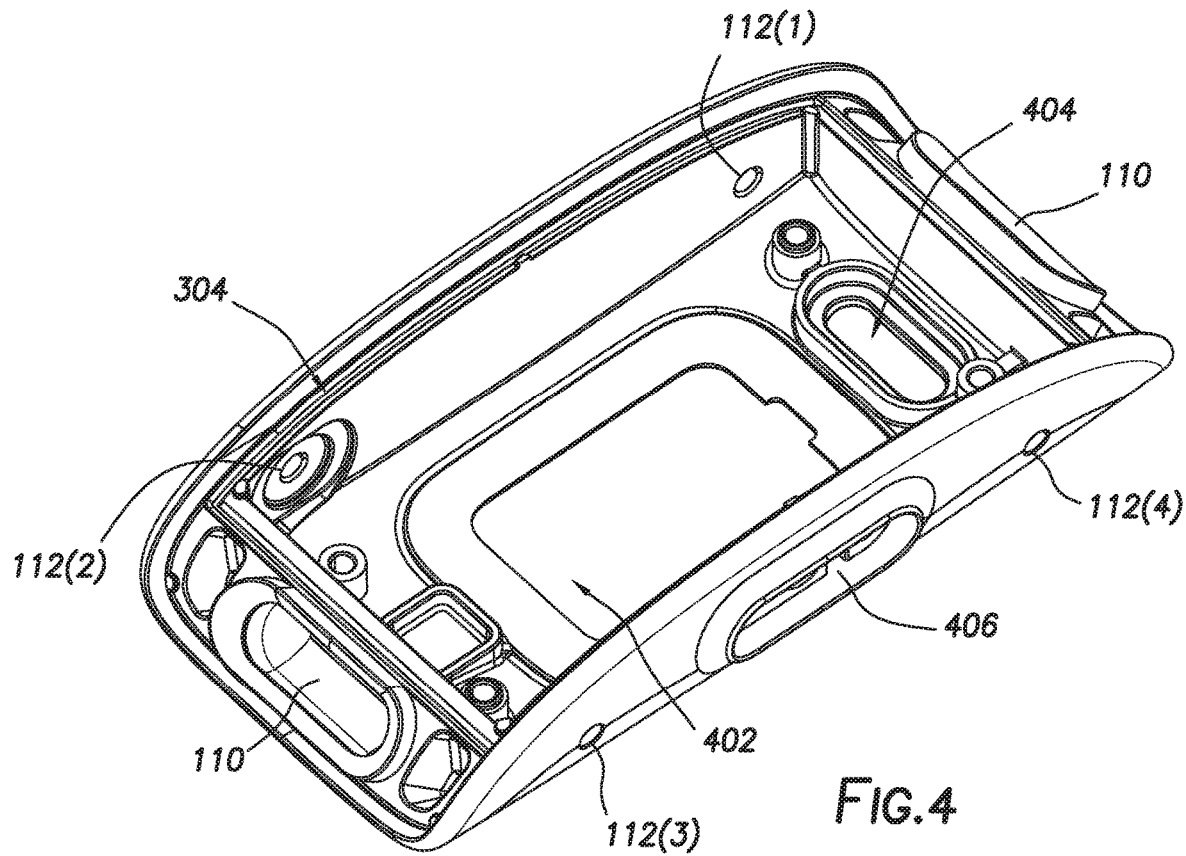
FIG. 4 is a perspective view of the housing of the wearable device, according to one implementation.

FIG. 4 is a perspective view of the housing 102 of the wearable device 100, according to one implementation. The receptacles 110 and the groove 304 are visible. Also shown are the apertures 112(1)-(4) on the sides of the housing 102. A sensor window aperture 402 is shown in the bottom of the housing 102. A contact aperture 404 is shown in the bottom of the housing, proximate to one end of the housing 102. A button aperture 406 is shown on a side of the housing 102 between apertures 112(3) and 112(4).

Figure 5:
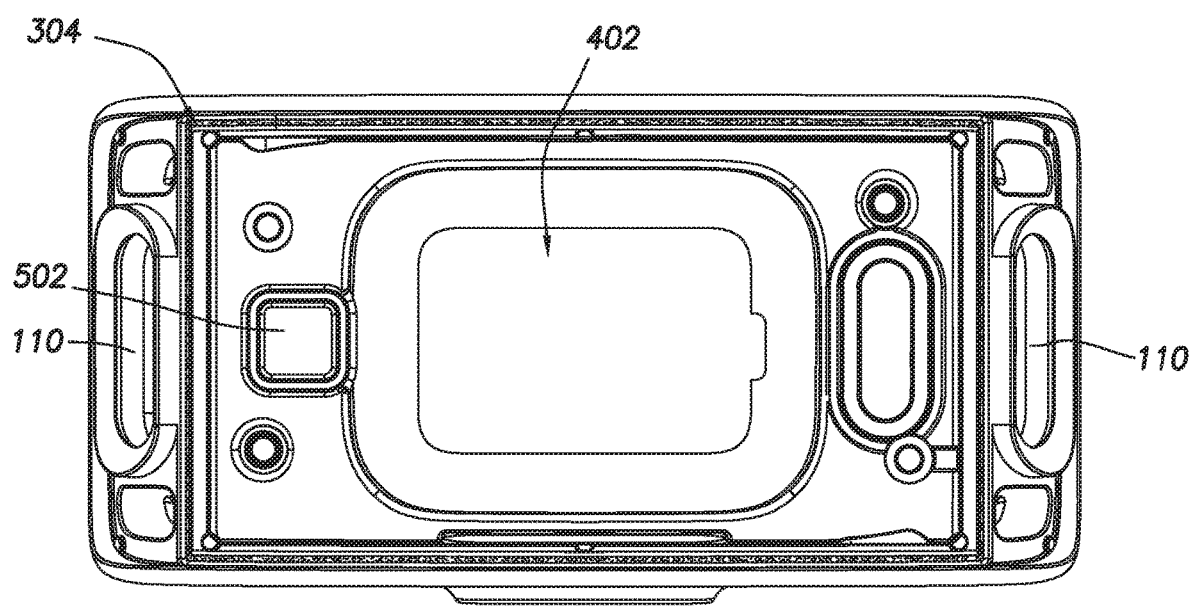
FIG. 5 is a plan view of the housing of the wearable device, according to one implementation.

FIG. 5 is a plan view of the housing 102 of the wearable device 100, according to one implementation. In this view a mounting feature 502 is shown. For example, a temperature sensor may be mounted at the mounting feature 502. The temperature sensor may provide information such as the temperature of the user's body as transferred through the portion of the housing 102 that is proximate to the mounting feature 502.

Figure 6A:
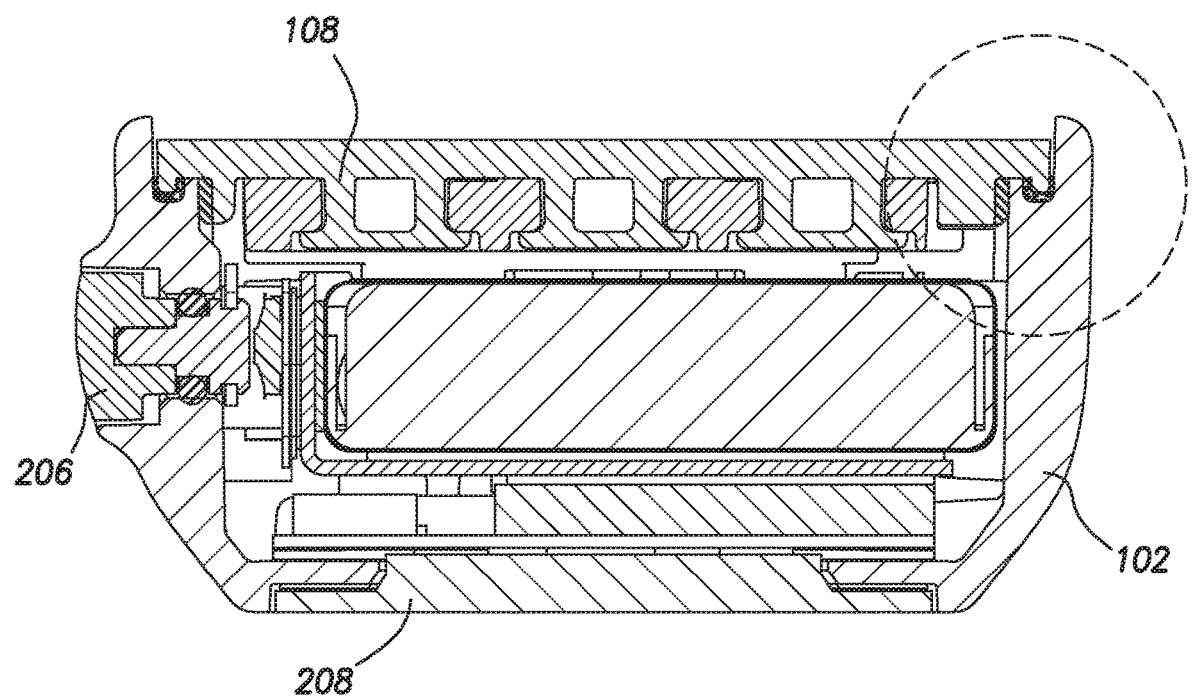
FIGS. 6A and 6B depict a cross sectional view of the housing including an enlargement of an interface between the upper cover and the housing, according to one implementation.
Figure 6B:
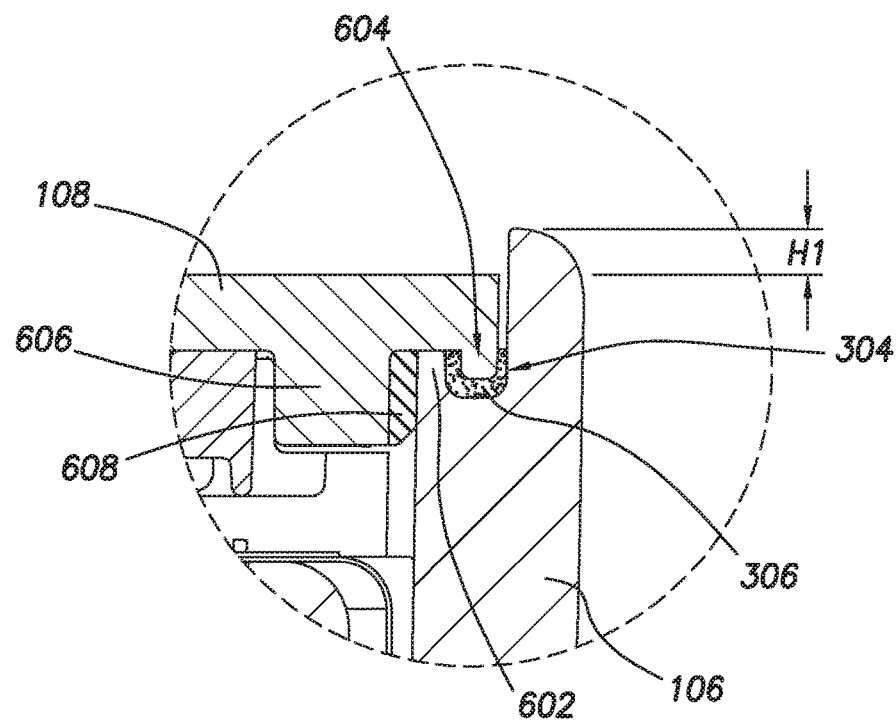

FIGS. 6A and 6B depict a cross-sectional view of the housing 102 along line A-A (as shown in FIG. 1) including an enlargement in FIG. 6B of an interface between the upper cover 108 and the housing 102, according to one implementation. FIG. 6A shows the cross section including the button 206, the housing 102, and the upper cover 108 joined to the housing 102. Also visible is the sensor window 208 installed within the sensor window aperture 402.

FIG. 6B shows an enlargement of a portion of the interface between the upper cover 108 and the housing 102. The housing 102 comprises a groove 304 having a lip 602. Within the groove 304 is the adhesive 306. The upper cover 108 includes a ridge 604 that is configured to fit within the groove 304. When installed, a portion of the ridge 604 comes into contact with the adhesive 306. The adhesive 306 joins the ridge 604 of the upper cover 108 to the housing 102. The adhesive 306 may form a seal to prevent the outside environment from reaching the interior of the housing 102. The lip 602 may act as a hard stop with respect to the upper cover 108.

In some implementations the upper cover 108 may include a second ridge 606 that is arranged to be adjacent to the lip 602 of the housing 102 when joined. A gasket 608 may be placed between the lip 602 and the second ridge 606 to provide an additional seal.

Figure 7:
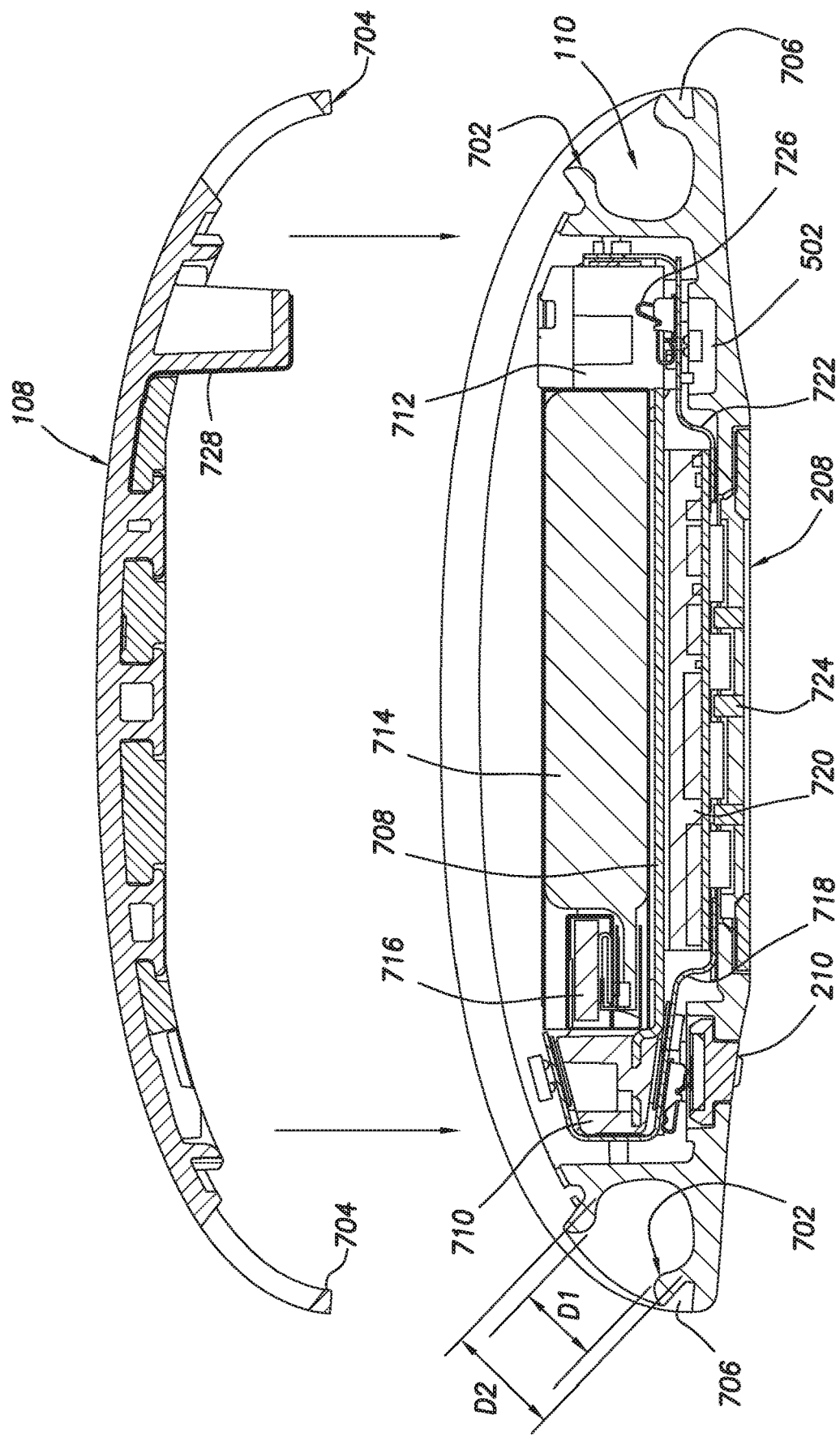
FIG. 7 is a cross sectional view of the housing, according to one implementation.

FIG. 7 is a cross sectional view of the housing 102 along line B-B (as shown in FIG. 1.), according to one implementation. In this view the upper cover 108 is shown separate from the housing 102.

The receptacles 110 are visible here. Each receptacle 110 has a retention ridge 702 proximate to the entry of the receptacle 110. In another implementation other engagement features may be used. For example, teeth may extend from the housing 102. The opening of the receptacle 110, the retention ridge 702, and the interior cavity of the receptacle 110 may be rounded or otherwise avoid sharp edges. Rounding of these features may facilitate controlled installation and removal of the protrusion 120 and may also improve lifespan of the protrusion 120 by preventing tearing.

The first distance D1 indicates the maximum width of the opening in the receptacle 110, as constrained by the retention ridge 702 or other feature. The second distance D2 indicates the maximum interior width of the receptacle 110 at the widest point of the interior space within the receptacle 110.

Due to the constriction in the receptacle 110, the first distance D1 is less than the second distance D2.

The upper cover 108 may include a first lip 704 and a second lip 704. The first lip 704 may be proximate to a first end of the upper cover 108 while the second lip 704 may be proximate to a second end of the upper cover 108. The first lip 704 and the second lip 704 extend from an inside surface of the upper cover 108. For example, in cross section the upper cover 108 may resemble a "C".

The housing 102 may also include one or more recesses 706. For example, the housing 102 may include a first recess 706 that is proximate to the first end the housing 102 and a second recess 706 that is proximate to the second end of the housing 102. The recess 706 is configured to accept the corresponding lip 704 and retain the upper cover 108 to the housing 102. For example, during assembly, the adhesive 306 is placed within the groove 304 and the upper cover 108 is moved into contact with the housing 102. Upon application of a force bringing the upper cover 108 and the housing 102 together, the ridge 604 enters the groove 304 and the first lip 704 enters the first recess 706 and the second lip 704 enters the second recess 706.

A metal chassis 708 is also shown. Various components may be mounted to the metal chassis 708. A first end of the metal chassis 710 and a second end of the metal chassis 712 may include features to facilitate mounting of other components. For example, the metal chassis 708 may include holes that permit the passage of a mechanical fastener such as a screw.

A battery 714 may be placed within the housing 102. The battery 714 may be used to provide electrical power to the components of the wearable device 100. The battery 714 may be rechargeable. A battery contact block 716 provides electrical connections between contacts on the battery 714 and the electronics of the wearable device 100. A flexible printed circuit (FPC) 718 provides one or more electrical traces to transfer one or more of power or data between components of the wearable device 100.

The wearable device 100 may utilize a system in package (SIP) construction, as shown with the SIP 720. The SIP 720 may comprise a processor, memory, power conditioning, or other components. The FPC 718 or other FPCs, wiring harnesses, and so forth may be used to interconnect the components in the wearable device 100.

An FPC 722 may be used as a transmission line to transfer radio frequency signals between the SIP 720 and one or more antenna contacts 726. When the upper cover 108 is installed on the housing 102 the antenna contacts 726 provide an electrical connection between the FPC 722 and a portion of an antenna trace 728. The antenna trace 728 may extend along a portion of an inner surface of the upper cover 108.

Also shown in this view is a window barrier 724 that is located between the sensor window 208 and the interior of the housing 102. For example, the electronics in the wearable device 100 may include an optical heart rate monitor that uses an LED to emit light and a photodetector to detect the light reflected or scattered by the arm of the user. The window barrier 724 may provide an opaque barrier between the LED and the photodetector to prevent the emitted light from intruding on and saturating the photodetector. The window barrier 724 also provides mechanical support to the sensor window 208.

Also shown are the contacts 210.

Figure 8:
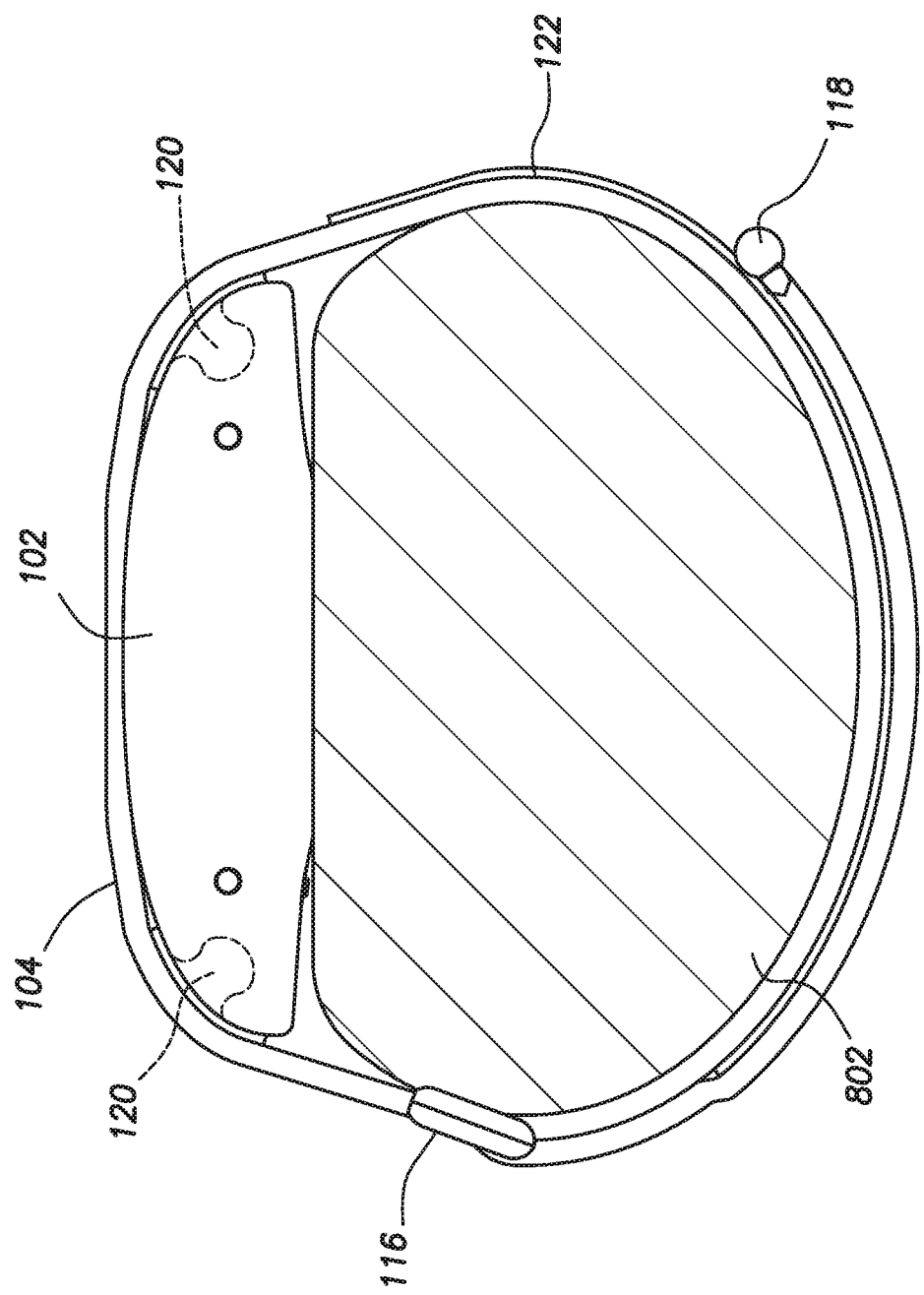
FIG. 8 depicts a view of the wearable device as worn by a user, according to one implementation.

FIG. 8 depicts a view of the wearable device 100 as worn by a user, according to one implementation. In this view a portion of the user's wrist 802 is shown, with the band 104 wrapped around the wrist 802.

Figure 9:
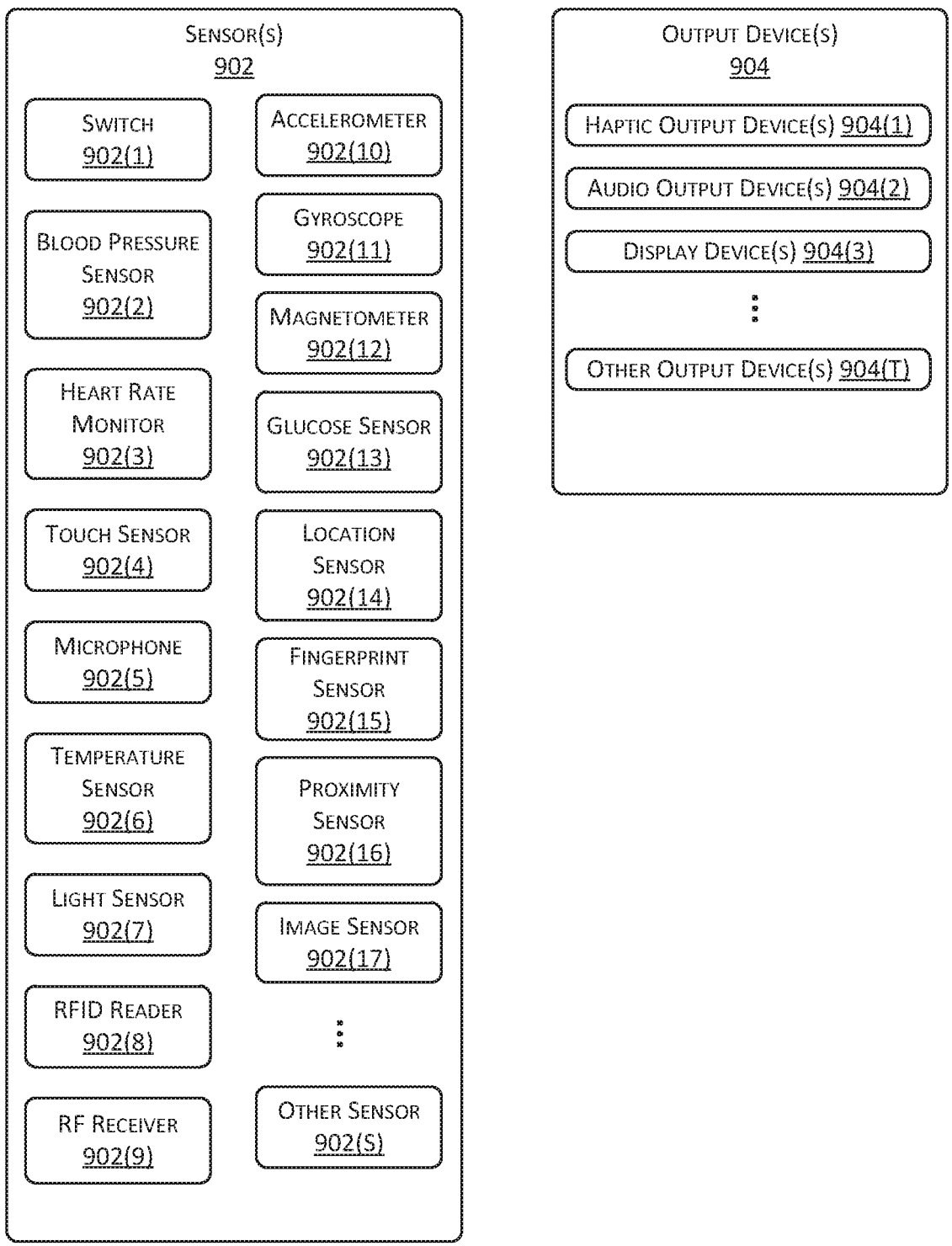
FIG. 9 illustrates a block diagram of sensors and output devices that the wearable device may utilize, according to one implementation.

FIG. 9 illustrates a block diagram of sensors 902 and output devices 904 that the wearable device 100 may utilize, according to one implementation. The sensors 902 may generate sensor data during operation.

The one or more sensors 902 may be integrated with or internal to the wearable device 100. For example, one or more of the sensors 902 may be built-in to the wearable device 100 during manufacture. In another example, one or more of the sensors 902 or a portion thereof may be incorporated into a band 104. In other implementations, the sensors 902 may be part of another device. For example, the sensors 902 may comprise a device external to, but in communication with, the wearable device 100 using Bluetooth, Wi-Fi, 3G, 4G, LTE, ZigBee, Z-Wave, or another wireless or wired communication technology.

The one or more sensors 902 may include one or more switches 902(1) that are configured to accept input from the user. The switches 902(1) may comprise mechanical, capacitive, optical, or other mechanisms. For example, the switches 902(1) may comprise mechanical switches configured to accept an applied force as transferred by the button 206 to generate an input signal.

A blood pressure sensor 902(2) may be configured to provide sensor data that is indicative of the user's blood pressure. For example, the blood pressure sensor 902(2) may comprise a camera that acquires images of blood vessels and determines the blood pressure by analyzing the changes in diameter of the blood vessels over time. In another example, the blood pressure sensor 902(2) may comprise a sensor transducer that is in contact with the skin of the user that is proximate to a blood vessel.

A heart rate monitor 902(3) may be configured to provide sensor data that is indicative of a cardiac pulse rate and data indicative of oxygen saturation of the user's blood. For example, an optical heart rate monitor 902(3) may use one or more light emitting diodes (LEDs) and corresponding detectors to determine changes in apparent color of the blood of the user resulting from oxygen binding with hemoglobin in the blood, providing information about oxygen saturation. Changes over time in apparent reflectance of light emitted by the LEDs may be used to determine cardiac pulse.

The sensors 902 may include one or more touch sensors 902(4). The touch sensors 902(4) may use resistive, capacitive, surface capacitance, projected capacitance, mutual capacitance, optical, Interpolating Force-Sensitive Resistance (IFSR), or other mechanisms to determine the position of a touch or near-touch of the user. For example, the IFSR may comprise a material configured to change electrical resistance responsive to an applied force. The location within the material of that change in electrical resistance may indicate the position of the touch.

One or more microphones 902(5) may be configured to acquire information about sound present in the environment. In some implementations, a plurality of microphones 902(5) may be used to form a microphone array. The microphone array may implement beamforming techniques to provide for directionality of gain.

A temperature sensor (or thermometer) 902(6) may provide information indicative of a temperature of an object. The temperature sensor 902(6) in the wearable device 100 may be configured to measure ambient air temperature proximate to the user, the body temperature of the user, and so forth. The temperature sensor 902(6) may comprise a silicon bandgap temperature sensor, thermistor, thermocouple, or other device. In some implementations, the temperature sensor 902(6) may comprise an infrared detector configured to determine temperature using thermal radiation. For example, the temperature sensor 902(6) may be mounted on the housing 102 within the mounting feature 502.

The sensors 902 may include one or more light sensors 902(7). The light sensors 902(7) may be configured to provide information associated with ambient lighting conditions such as a level of illumination. The light sensors 902(7) may be sensitive to wavelengths including, but not limited to, infrared, visible, or ultraviolet light. In contrast to a camera, the light sensor 902(7) may typically provide a sequence of amplitude (magnitude) samples and color data while the camera provides a sequence of two-dimensional frames of samples (pixels).

One or more radio frequency identification (RFID) readers 902(8), near field communication (NFC) systems, and so forth, may also be included as sensors 902. The user, objects around the wearable device 100, locations within a building, and so forth, may be equipped with one or more radio frequency (RF) tags. The RF tags are configured to emit an RF signal. In one implementation, the RF tag may be an RFID tag configured to emit the RF signal upon activation by an external signal. For example, the external signal may comprise a RF signal or a magnetic field configured to energize or activate the RFID tag. In another implementation, the RF tag may comprise a transmitter and a power source configured to power the transmitter. For example, the RF tag may comprise a Bluetooth Low Energy (BLE) transmitter and battery. In other implementations, the tag may use other techniques to indicate its presence. For example, an acoustic tag may be configured to generate an ultrasonic signal, which is detected by corresponding acoustic receivers. In yet another implementation, the tag may be configured to emit an optical signal.

One or more RF receivers 902(9) may also be included as sensors 902. In some implementations, the RF receivers 902(9) may be part of transceiver assemblies. The RF receivers 902(9) may be configured to acquire RF signals associated with Wi-Fi, Bluetooth, ZigBee, Z-Wave, 3G, 4G, LTE, or other wireless data transmission technologies. The RF receivers 902(9) may provide information associated with data transmitted via radio frequencies, signal strength of RF signals, and so forth. For example, information from the RF receivers 902(9) may be used to facilitate determination of a location of the wearable device 100, and so forth.

The sensors 902 may include one or more accelerometers 902(10). The accelerometers 902(10) may provide information such as the direction and magnitude of an imposed acceleration, tilt relative to local vertical, and so forth. Data such as rate of acceleration, or determination of changes in direction, speed, tilt, and so forth, may be determined using the accelerometers 902(10).

A gyroscope 902(11) provides information indicative of rotation of an object affixed thereto. For example, the gyroscope 902(11) may indicate whether the device has been rotated, rate of rotation, direction of rotation, and so forth.

A magnetometer 902(12) may be used to determine an orientation by measuring ambient magnetic fields, such as the terrestrial magnetic field. For example, output from the magnetometer 902(12) may be used to determine whether the device containing the sensor 902, such as the wearable device 100, has changed orientation or otherwise moved. In other implementations, the magnetometer 902(12) may be configured to detect magnetic fields generated by another device.

A glucose sensor 902(13) may be used to determine a concentration of glucose within the blood or tissues of the user. For example, the glucose sensor 902(13) may comprise a near infrared spectroscope that determines a concentration of glucose or glucose metabolites in tissues. In another example, the glucose sensor 902(13) may comprise a chemical detector that measures presence of glucose or glucose metabolites at the surface of the user's skin.

A location sensor 902(14) is configured to provide information indicative of a location. The location may be relative or absolute. For example, a relative location may indicate "kitchen", "bedroom", "conference room", and so forth. In comparison, an absolute location is expressed relative to a reference point or datum, such as a street address, geolocation comprising coordinates indicative of latitude and longitude, grid square, and so forth. The location sensor 902 (14) may include, but is not limited to, radio navigation-based systems such as terrestrial or satellite-based navigational systems. The satellite-based navigation system may include one or more of a Global Positioning System (GPS) receiver, a Global Navigation Satellite System (GLONASS) receiver, a Galileo receiver, a BeiDou Navigation Satellite System (BDS) receiver, an Indian Regional Navigational Satellite System, and so forth. In some implementations, the location sensor 902(14) may be omitted or operate in conjunction with an external resource such as a cellular network operator providing location information, or Bluetooth beacons.

A fingerprint sensor 902(15) is configured to acquire fingerprint data. The fingerprint sensor 902(15) may use an optical, ultrasonic, capacitive, resistive, or other detector to obtain an image or other representation of features of a finger. For example, the fingerprint sensor 902(15) may comprise a capacitive sensor configured to generate an image of the fingerprint of the user.

A proximity sensor 902(16) may be configured to provide sensor data indicative of one or more of a presence or absence of an object, a distance to the object, or characteristics of the object. The proximity sensor 902(16) may use optical, electrical, ultrasonic, electromagnetic, or other techniques to determine a presence of an object. For example, the proximity sensor 902(16) may comprise a capacitive proximity sensor configured to provide an electrical field and determine a change in electrical capacitance due to presence or absence of an object within the electrical field.

An image sensor 902(17) comprises an imaging element to acquire images in visible light, infrared light, ultraviolet light, and so forth. For example, the image sensor 902(17) may comprise complementary metal oxide (CMOS) imaging element or a charge coupled device (CCD).

The sensors 902 may include other sensors 902(S) as well. For example, the other sensors 902(S) may include strain gauges, anti-tamper indicators, and so forth. For example, strain gauges or strain sensors may be embedded within the wearable device 100 and may be configured to provide information indicating that at least a portion of the wearable device 100 has been stretched or displaced such that the wearable device 100 may have been donned or doffed.

In some implementations, the sensors 902 may include hardware processors, memory, and other elements configured to perform various functions. Furthermore, the sensors 902 may be configured to communicate by way of a network or may couple directly with the other devices.

The wearable device 100 may include or may couple to one or more output devices 904. The output devices 904 are configured to generate signals which may be perceived by the user, detectable by the sensors 902, or a combination thereof.

Haptic output devices 904(1) are configured to provide a signal, which results in a tactile sensation to the user. The haptic output devices 904(1) may use one or more mechanisms such as electrical stimulation or mechanical displacement to provide the signal. For example, the haptic output devices 904(1) may be configured to generate a modulated electrical signal, which produces an apparent tactile sensation in one or more fingers of the user. In another example, the haptic output devices 904(1) may comprise piezoelectric or rotary motor devices configured to provide a vibration that may be felt by the user.

One or more audio output devices 904(2) are configured to provide acoustic output. The acoustic output includes one or more of infrasonic sound, audible sound, or ultrasonic sound. The audio output devices 904(2) may use one or more mechanisms to generate the acoustic output. These mechanisms may include, but are not limited to, the following: voice coils, piezoelectric elements, magnetostrictive elements, electrostatic elements, and so forth. For example, a piezoelectric buzzer or a speaker may be used to provide acoustic output by an audio output device 904(2).

The display devices 904(3) may be configured to provide output that may be seen by the user or detected by a light-sensitive detector such as the image sensor 902(17) or light sensor 902(7). The output may be monochrome or color. The display devices 904(3) may be emissive, reflective, or both. An emissive display device 904(3), such as using LEDs, is configured to emit light during operation. In comparison, a reflective display device 904(3), such as using an electrophoretic element, relies on ambient light to present an image. Backlights or front lights may be used to illuminate non-emissive display devices 904(3) to provide visibility of the output in conditions where the ambient light levels are low.

The display mechanisms of display devices 904(3) may include, but are not limited to, micro-electromechanical systems (MEMS), spatial light modulators, electroluminescent displays, quantum dot displays, liquid crystal on silicon (LCOS) displays, cholesteric displays, interferometric displays, liquid crystal displays, electrophoretic displays, LED displays, and so forth. These display mechanisms are configured to emit light, modulate incident light emitted from another source, or both. The display devices 904(3) may operate as panels, projectors, and so forth.

The display devices 904(3) may be configured to present images. For example, the display devices 904(3) may comprise a pixel-addressable display. The image may comprise at least a two-dimensional array of pixels or a vector representation of an at least two-dimensional image.

In some implementations, the display devices 904(3) may be configured to provide non-image data, such as text or numeric characters, colors, and so forth. For example, a segmented electrophoretic display device 904(3), segmented LED, and so forth, may be used to present information such as letters or numbers. The display devices 904(3) may also be configurable to vary the color of the segment, such as using multicolor LED segments.

Other output devices 904(T) may also be present.

Figure 10:
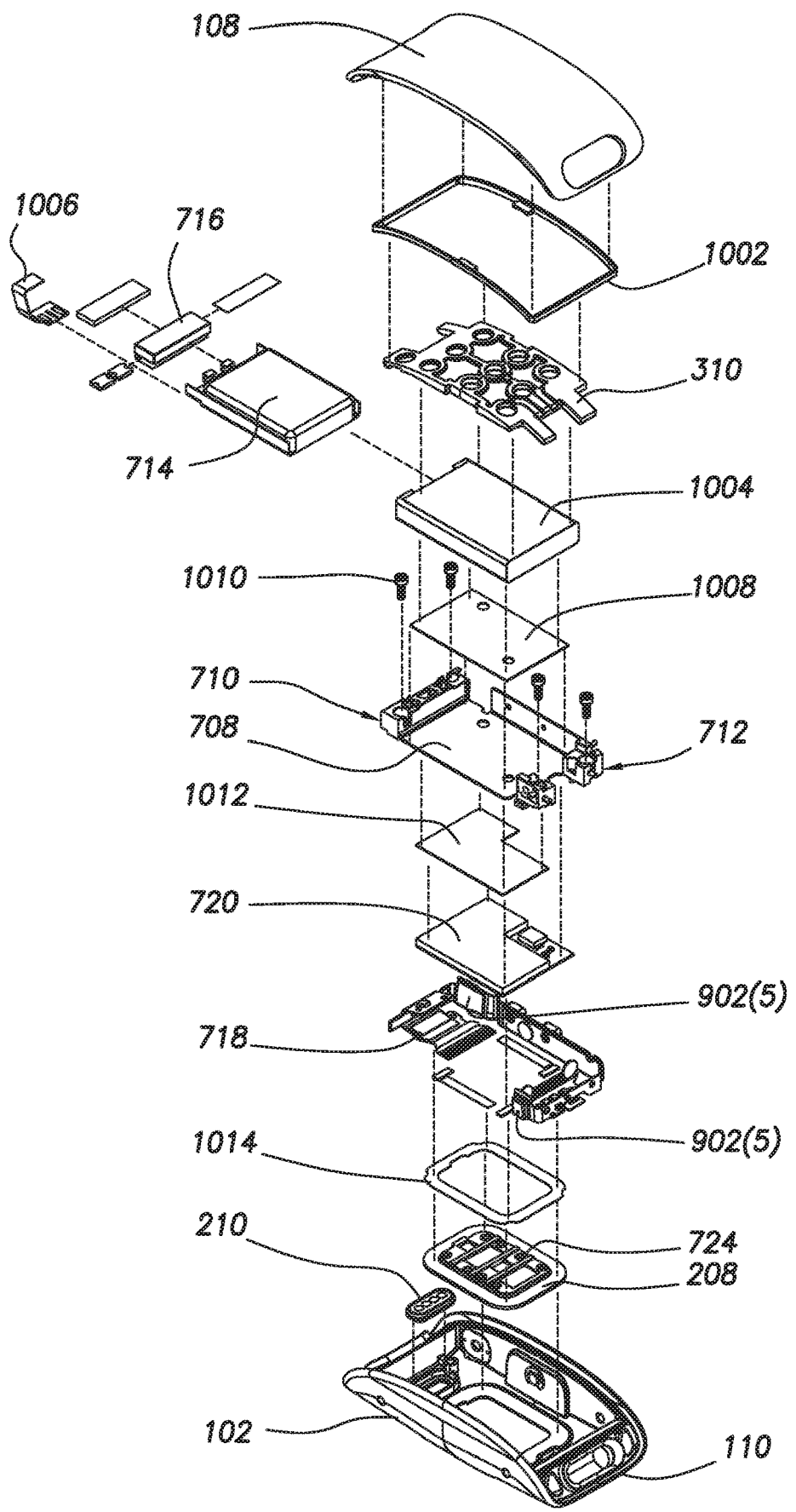
FIG. 10 is a view of components in the housing of the wearable device, according to one implementation.

FIG. 10 is a view of components in the housing 102 of the wearable device 100, according to one implementation. The top cover 108 is shown. A frame 1002 is shown that assists in alignment and retention of the internal stiffener 310.

The battery 714 may be arranged within a battery cover 1004. For example, the battery cover 1004 may comprise a mylar sheath that is arranged around at least a portion of the battery 714.

A battery flexible printed circuit (FPC) 1006 is shown that provides electrical connectivity between the battery contact block 716 and the SIP 720.

An adhesive 1008 affixes the battery cover 1004 to an upper side of the metal chassis 708. For example, the adhesive 1008 may comprise a sheet or layer of a pressure sensitive adhesive (PSA).

Mechanical fasteners 1010, such as screws, are shown that join the metal chassis 708 to the housing 102. In other implementations other techniques may be used to join the metal chassis 708 to the housing 102. For example, the metal chassis 708 may include one or more mechanical engagement features such as ridges, tabs, and so forth that engage features on the housing 102.

An adhesive 1012 affixes a lower side of the metal chassis 708 to the SIP 720. For example, the adhesive 1012 may comprise a sheet or layer of PSA.

Also shown in this figure is the FPC 718 that provides connectivity between the various components in the wearable device 100. For example, the FPC 718 extends around a perimeter of an interior of the housing 102. The SIP 720, one or more sensors 902, output devices 904 such as LEDs, and so forth may be connected to the FPC 718. For example, the microphones 902(5) are shown attached to the FPC 718.

An adhesive 1014 affixes an upper side of the sensor window 208 to a lower side of the metal chassis 708. For example, the adhesive 1014 may comprise a sheet or layer of PSA.

The window barrier 724 arranged on an upper side of the sensor window 208 is also shown. The contacts 210 are also depicted.

One of the receptacles 110 in the housing 102 are also shown. While a pair of receptacles 110 are depicted, in other implementations other arrangements may be used. For example, the housing 102 may comprise a single receptacle 110 while the band 104 features a corresponding single protrusion 120. In another example, the housing 102 may comprise three receptacles 110 while the band 104 features three corresponding protrusions 120.

Figure 11:
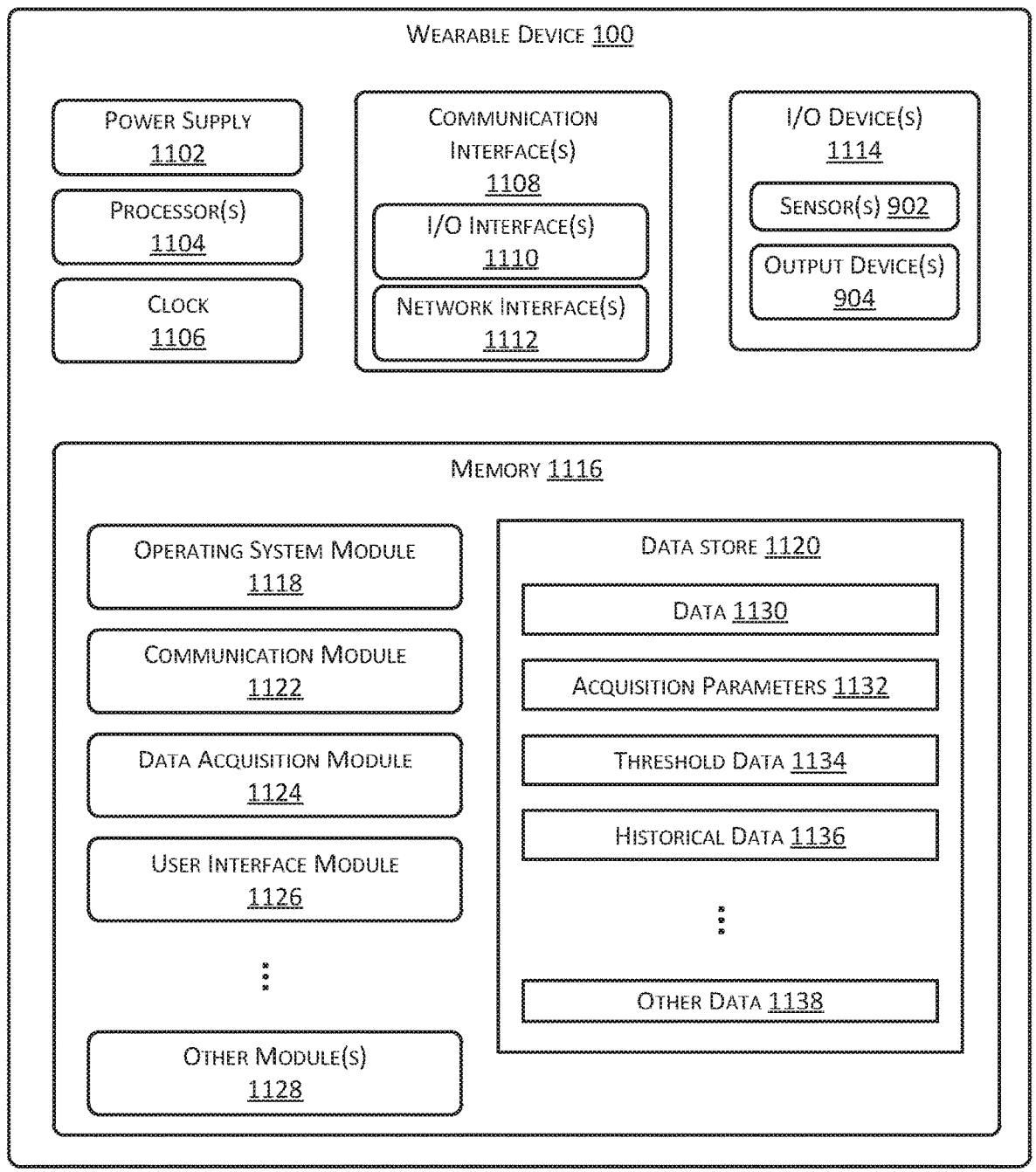
FIG. 11 illustrates a block diagram of some components of the wearable device, according to one implementation.

FIG. 11 illustrates a block diagram of some components of the wearable device 100, according to one implementation.

One or more power supplies 1102 are configured to provide electrical power suitable for operating the components in the wearable device 100. In some implementations, the power supply 1102 may comprise a rechargeable battery, fuel cell, photovoltaic cell, power conditioning circuitry, wireless power receiver, thermocouple, and so forth.

The wearable device 100 may include one or more hardware processors 1104 (processors) configured to execute one or more stored instructions. The processors 1104 may comprise one or more cores. One or more clocks 1106 may provide information indicative of date, time, ticks, and so forth. For example, the processor 1104 may use data from the clock 1106 to generate a timestamp, trigger a preprogrammed action, and so forth.

The wearable device 100 may include one or more communication interfaces 1108 such as input/output (I/O) interfaces 1110, network interfaces 1112, and so forth. The communication interfaces 1108 enable the wearable device 100, or components thereof, to communicate with other devices or components. The communication interfaces 1108 may include one or more I/O interfaces 1110. The I/O interfaces 1110 may comprise interfaces such as Inter-Integrated Circuit (I2C), Serial Peripheral Interface bus (SPI), Universal Serial Bus (USB) as promulgated by the USB Implementers Forum, RS-232, and so forth.

The I/O interface(s) 1110 may couple to one or more I/O devices 1114. The I/O devices 1114 may include input devices such as one or more of the sensors 902. The I/O devices 1114 may also include output devices 904 such as one or more of an audio output device 904(2), a display device 904(3), and so forth. In some embodiments, the I/O devices 1114 may be physically incorporated with the wearable device 100 or may be externally placed.

The network interfaces 1112 are configured to provide communications between the wearable device 100 and other devices, such as the sensors 902, routers, access devices, and so forth. The network interfaces 1112 may include devices configured to couple to wired or wireless personal area networks (PANs), local area networks (LANs), wide area networks (WANs), and so forth. For example, the network interfaces 1112 may include devices compatible with Ethernet, Wi-Fi, Bluetooth, ZigBee, 4G, 5G, LTE, and so forth.

The wearable device 100 may also include one or more buses or other internal communications hardware or software that allow for the transfer of data between the various modules and components of the wearable device 100.

As shown in FIG. 11, the wearable device 100 includes one or more memories 1116. The memory 1116 comprises one or more computer-readable storage media (CRSM). The CRSM may be any one or more of an electronic storage medium, a magnetic storage medium, an optical storage medium, a quantum storage medium, a mechanical computer storage medium, and so forth. The memory 1116 provides storage of computer-readable instructions, data structures, program modules, and other data for the operation of the wearable device 100. A few example functional modules are shown stored in the memory 1116, although the same functionality may alternatively be implemented in hardware, firmware, or as a system on a chip (SOC).

The memory 1116 may include at least one operating system (OS) module 1118. The OS module 1118 is configured to manage hardware resource devices such as the I/O interfaces 1110, the network interfaces 1112, the I/O devices 1114, and provide various services to applications or modules executing on the processors 1104. The OS module 1118 may implement a variant of the FreeBSD operating system as promulgated by the FreeBSD Project; other UNIX or UNIX-like operating system; a variation of the Linux operating system as promulgated by Linus Torvalds; the Windows operating system from Microsoft Corporation of Redmond, Wash., USA; the Android operating system from Google Corporation of Mountain View, Calif., USA; the iOS operating system from Apple Corporation of Cupertino, Calif., USA; or other operating systems.

Also stored in the memory 1116 may be a data store 1120 and one or more of the following modules. These modules may be executed as foreground applications, background tasks, daemons, and so forth. The data store 1120 may use a flat file, database, linked list, tree, executable code, script, or other data structure to store information. In some implementations, the data store 1120 or a portion of the data store 1120 may be distributed across one or more other devices.

A communication module 1122 may be configured to establish communications with one or more of other devices, the sensors 902, and so forth. The communications may be authenticated, encrypted, and so forth. The communication module 1122 may also control the communication interfaces 1108.

The memory 1116 may also store a data acquisition module 1124. The data acquisition module 1124 is configured to acquire sensor data. In some implementations the data acquisition module 1124 may be configured to operate the one or more sensors 902, the microphone array 902(5), and so forth. For example, the data acquisition module 1124 may determine that the sensor data satisfies a trigger event. The trigger event may comprise values of sensor data for one or more sensors 902 exceeding a threshold value.

In another example, the data acquisition module 1124 on the wearable device 100 may receive instructions from another device, such as a smartphone, to acquire sensor data at a specified interval, at a scheduled time, and so forth.

A user interface module 1126 provides a user interface using one or more of the I/O devices 1114. The user interface module 1126 may be used to obtain input from the user, present information to the user, and so forth. For example, the user interface module 1126 may accept input from the user via the switch 902(1) and use the display device 904(3) such as an LED to provide output to the user.

One or more other modules 1128 may also be stored in the memory 1116.

Data 1130 may be stored in the data store 1120. For example, the data 1130 may comprise the sensor data, user preferences, and so forth.

One or more acquisition parameters 1132 may be stored in the memory 1116. The acquisition parameters 1132 may specify operation of the data acquisition module 1124, such as data sample rate, sample frequency, scheduling, and so forth.

Threshold data 1134 may be stored in the memory 1116. For example, the threshold data 1134 may specify one or more thresholds used by the data acquisition module 1124 to determine whether sensor data is to be retained or discarded.

The wearable device 100 may maintain historical data 1136. The historical data 1136 may be used to provide information about trends or changes over time. For example, the historical data 1136 may comprise data indicative of movement as measured by the accelerometer 902(10) over several hours or days.

Other data 1138 may also be stored in the data store 1120.

The wearable device 100 may operate in conjunction with one or more other devices. For example, sensor data may be sent from the wearable device 100 to a smartphone, server, or other computing device for processing.

Specific physical embodiments as described in this disclosure are provided by way of illustration and not necessarily as a limitation. Those having ordinary skill in the art readily recognize that alternative implementations, variations, and so forth may also be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features, structures, and acts are disclosed as exemplary forms of implementing the claims.

Processes discussed herein may be implemented in hardware, software, or a combination thereof. In the context of software, the described operations represent computer-executable instructions stored on one or more non-transitory computer-readable storage media that, when executed by one or more processors, perform the recited operations. Generally, computer-executable instructions include routines, programs, objects, components, data structures, and the like that perform particular functions or implement particular abstract data types. Those having ordinary skill in the art will readily recognize that certain steps or operations illustrated in the figures above may be eliminated, combined, or performed in an alternate order. Any steps or operations may be performed serially or in parallel. Furthermore, the order in which the operations are described is not intended to be construed as a limitation.

Embodiments may be provided as a software program or computer program product including a non-transitory computer-readable storage medium having stored thereon instructions (in compressed or uncompressed form) that may be used to program a computer (or other electronic device) to perform processes or methods described herein. The computer-readable storage medium may be one or more of an electronic storage medium, a magnetic storage medium, an optical storage medium, a quantum storage medium, and so forth. For example, the computer-readable storage media may include, but is not limited to, hard drives, optical disks, read-only memories (ROMs), random access memories (RAMs), erasable programmable ROMs (EPROMs), electrically erasable programmable ROMs (EEPROMs), flash memory, magnetic or optical cards, solid-state memory devices, or other types of physical media suitable for storing electronic instructions. Further, embodiments may also be provided as a computer program product including a transitory machine-readable signal (in compressed or uncompressed form). Examples of transitory machine-readable signals, whether modulated using a carrier or unmodulated, include, but are not limited to, signals that a computer system or machine hosting or running a computer program can be configured to access, including signals transferred by one or more networks. For example, the transitory machine-readable signal may comprise transmission of software by the Internet.

Separate instances of these programs can be executed on or distributed across any number of separate computer systems. Thus, although certain steps have been described as being performed by certain devices, software programs, processes, or entities, this need not be the case, and a variety of alternative implementations will be understood by those having ordinary skill in the art.

Additionally, those having ordinary skill in the art will readily recognize that the techniques described above can be utilized in a variety of devices, environments, and situations. Although the subject matter has been described in language specific to structural features or methodological acts, it is to be understood that the subject matter defined in the appended claims is not necessarily limited to the specific features or acts described. Rather, the specific features and acts are disclosed as illustrative forms of implementing the claims.

What is claimed is:

1. A wearable device comprising:
   a housing, comprising:
      a first surface that is distal to a user during wear;
      a second surface that is proximate to the user during wear;
      a first receptacle proximate to a first end of the first surface, wherein the first receptacle has a first opening with a first distance and a first interior space with a second distance, wherein the first distance is less than the second distance; and
      a second receptacle proximate to a second end of the first surface, wherein the second receptacle has a second opening with a third distance and a second interior space with a fourth distance, wherein the third distance is less than the fourth distance; and
   a band comprising:
      a first member comprising:
         a first end;
         a second end;
         a third surface that is distal to the user and the first surface during wear; and
         a fourth surface that is proximal to the user and the first surface during wear;
      a first protrusion extending from the fourth surface at a first location on the first member, wherein the first protrusion has a first tip with a fifth distance that is greater than the first distance; and
      a second protrusion extending from the fourth surface at a second location on the first member, wherein the second protrusion has a second tip with a sixth distance that is greater than the third distance.

2. The wearable device of claim 1, wherein at least a portion of the first surface is in contact with the fourth surface of at least a portion of the first member that is between the first protrusion and the second protrusion.

3. The wearable device of claim 1, wherein:
   at least a portion of the first member that is between the first location and the second location is elastomeric; and
   a seventh distance extending between the first receptacle and the second receptacle along the first surface of the housing is greater than an eighth distance extending between the first location and the second location when the at least a portion of the first member is not under tension.

4. The wearable device of claim 1, wherein:
   the first protrusion and the second protrusion comprise an elastomeric material;
   the fifth distance is at least 15% greater than the first distance; and
   the sixth distance is at least 15% greater than the third distance.

5. The wearable device of claim 1, wherein:
   at least a portion of the first tip is compressed by the first receptacle after insertion of the first tip into the first receptacle; and
   at least a portion of the second tip is compressed by the second receptacle after insertion of the second tip into the second receptacle.

6. The wearable device of claim 1, wherein:
   the first protrusion and the second protrusion comprise an elastomeric material;
   the fifth distance is greater than the second distance; and
   the sixth distance is greater than the fourth distance.

7. The wearable device of claim 1, wherein the first protrusion and the second protrusion comprise an elastomeric material having a hardness as measured using a durometer with a Shore A reading of between 70 and 90.

8. The wearable device of claim 1, wherein the first member, the first protrusion, and the second protrusion comprise a unitary piece of elastomeric material.

9. The wearable device of claim 1, wherein at least a portion of the first member that is between the first location and the second location comprises one or more of a transparent material or one or more holes.

10. The wearable device of claim 1, the housing further comprising:
   a first recess arranged between the first end and the first receptacle;
   a second recess arranged between the second end and the second receptacle;
   a groove extending around a perimeter of an opening in the housing;

an adhesive within the groove; and
a cover comprising:
  a first end;
  a second end;
  a fifth surface proximate to the user during wear;
  a sixth surface distal to the user during wear;
  a first lip proximate to the first end of the cover on the fifth surface, wherein the first lip is retained within the first recess;
  a second lip proximate to the second end of the cover on the fifth surface, wherein the second lip is retained within the second recess; and
  a ridge along a perimeter of the fifth surface, wherein at least a portion of the ridge is arranged within the groove and is in contact with at least a portion of the adhesive.

11. The wearable device of claim 1, the housing further comprising:
  a sensor window aperture in the second surface;
  a sensor window affixed to the second surface at the sensor window aperture; and
  a sensor having a field of view that passes through the sensor window.

12. A device comprising:
  a housing, comprising:
    a first surface distal to a user during wear;
    a second surface proximate to the user during wear;
    a sensor window in the second surface; and
    a first receptacle proximate to a first end of the first surface, wherein the first receptacle has a first opening with a first distance and a first interior space with a second distance, wherein the first distance is less than the second distance; and
  a band comprising:
    a first member comprising:
      a first end,
      a second end,
      a third surface that is distal to the user during wear, and
      a fourth surface that is proximate to the user during wear; and
    a first protrusion extending from the fourth surface at a first location on the first member, wherein the first protrusion has a first portion with a third distance that is greater than the first distance.

13. The device of claim 12, the housing further comprising:
  a first recess arranged between the first end of the first surface and the first receptacle;
  a groove extending around a perimeter of an opening in the housing;
  an adhesive within the groove; and
  a cover comprising:
    a first end;
    a second end;
    a fifth surface proximate to the user during wear;
    a sixth surface distal to the user during wear;
    a first lip proximate to the first end of the cover on the fifth surface, wherein the first lip is retained within the first recess; and
    a ridge along a perimeter of the fifth surface, wherein at least a portion of the ridge is arranged within the groove and is in contact with at least a portion of the adhesive.

14. The device of claim 12, further comprising:
a second receptacle proximate to a second end of the first surface, wherein the second receptacle has a second opening with a fourth distance and a second interior space with a fifth distance, wherein the fourth distance is less than the fifth distance; and
wherein the band further comprises:
  a second protrusion extending from the fourth surface at a second location on the first member, wherein the second protrusion has a second portion with a sixth distance that is greater than the fourth distance.

15. The device of claim 14, wherein the first protrusion and the second protrusion comprise an elastomeric material.

16. The device of claim 14, wherein:
at least a portion of the first member that is between the first location and the second location is elastomeric; and
a seventh distance extending between the first receptacle and the second receptacle along the first surface of the housing is greater than an eighth distance extending between the first location and the second location when the at least a portion of the first member is not under tension.

17. The device of claim 14, wherein at least a portion of the first member that is between the first location and the second location comprises one or more of a transparent material or one or more holes.

18. The device of claim 14, wherein the first member, the first protrusion, and the second protrusion comprise a unitary piece of elastomeric material.

19. A device comprising:
  a housing comprising;
    a first surface distal to a user during wear;
    a second surface proximate to the user during wear;
    a sensor window on the second surface of the housing; and
    a first receptacle proximate to a first end of the first surface, wherein the first receptacle has a first opening with a first distance and a first interior space with a second distance, wherein the first distance is less than the second distance; and
  a band comprising:
    a flexible member comprising:
      a first end,
      a second end,
      a third surface that is distal to the user during wear, and
      a fourth surface that is proximate to the user during wear;
    a first protrusion extending from the fourth surface at a first location on the flexible member, wherein the first protrusion comprises an elastomeric material with a first enlarged tip that has an uncompressed size greater than the first opening of the first receptacle; and
    a second protrusion extending from the fourth surface at a second location on the flexible member, wherein the second protrusion comprises an elastomeric material with a second enlarged tip that has an uncompressed size greater than a second opening of a second receptacle.

20. The device of claim 19, wherein:
the housing further comprises:
  an optical heart rate monitor located within the housing and proximate to the sensor window;
  a groove extending around a perimeter of an upper portion of the housing;
  an adhesive within the groove; and an upper cover having a ridge along an underside, wherein at least a portion of the ridge fits within the groove and comes into contact with the adhesive; and the band further comprising:
- a rigid loop attached to the first end of the flexible member;
- a first section that is proximate to the second end and attached to the third surface of the flexible member, wherein the first section comprises a plurality of hooks; and
- a second section comprising a plurality of loops extending from the third surface of the flexible member.

\* \* \* \* \*